United States Patent [19]

Wainwright

[11] Patent Number: 4,682,156
[45] Date of Patent: Jul. 21, 1987

[54] SOLVENT DETECTOR

[75] Inventor: H. Kent Wainwright, Laramie, Wyo.

[73] Assignee: In-Situ, Inc., Laramie, Wyo.

[21] Appl. No.: 667,877

[22] Filed: Nov. 2, 1984

[51] Int. Cl.$^4$ ............................................. G08B 21/00
[52] U.S. Cl. ........................................ 340/603; 73/40;
177/46; 200/61.04; 340/605; 340/613; 340/666
[58] Field of Search ............... 340/603, 613, 665, 666,
340/590, 605; 200/85 R, 61.2, 61.21, 61.83,
61.04; 177/45, 46, 50, 233; 116/215, 212, 283;
73/296, 40

[56] References Cited

U.S. PATENT DOCUMENTS

| | | | |
|---|---|---|---|
| 1,216,678 | 2/1917 | Ford | 340/624 X |
| 1,973,272 | 9/1934 | Sremec | 340/590 X |
| 2,670,194 | 2/1954 | Hansson | 177/45 X |
| 3,200,387 | 8/1965 | Loscher | 340/603 X |
| 3,720,797 | 3/1973 | Gunn et al. | 200/61.08 |
| 3,885,418 | 5/1975 | Kriebel | 73/61.1 R |
| 3,970,863 | 7/1976 | Kishikawa et al. | 307/116 |
| 4,131,773 | 12/1978 | Maham et al. | 200/61.05 |
| 4,202,203 | 5/1980 | Potter | 73/61.1 R |
| 4,305,068 | 12/1981 | Klein | 340/605 |
| 4,351,642 | 9/1982 | Bonavent et al. | 340/605 |

*Primary Examiner*—Charles A. Ruehl
*Assistant Examiner*—Daniel Myer
*Attorney, Agent, or Firm*—Sheridan, Ross & McIntosh

[57] ABSTRACT

An apparatus and method are provided for detecting solvents, including hydrocarbons. The apparatus includes a hydrocarbon-soluble plastic rod which interconnects a mass or weight and a weighing assembly. The weighing assembly is operatively joined to an alarm indicator, which is utilized to inform the user as to whether hydrocarbons are present. In a preferred arrangement, the weighing assembly is connected to a housing, which is joined to the top of a well casing provided in the ground. The plastic rod may be of any desired length, depending upon the depth of the well casing and where it is desired to check for hydrocarbons. When hydrocarbons are detected the plastic rod dissolves or separates causing movement of the weighing assembly and the alarm indicator so that a visual indication is provided that hydrocarbons are present. The apparatus further includes a mass catch assembly for maintaining connection between the mass and the housing after the plastic rod separates due to the presence of hydrocarbons. Additionally, the apparatus has a testing assembly which can be utilized by the user to check the operation of the apparatus.

27 Claims, 6 Drawing Figures

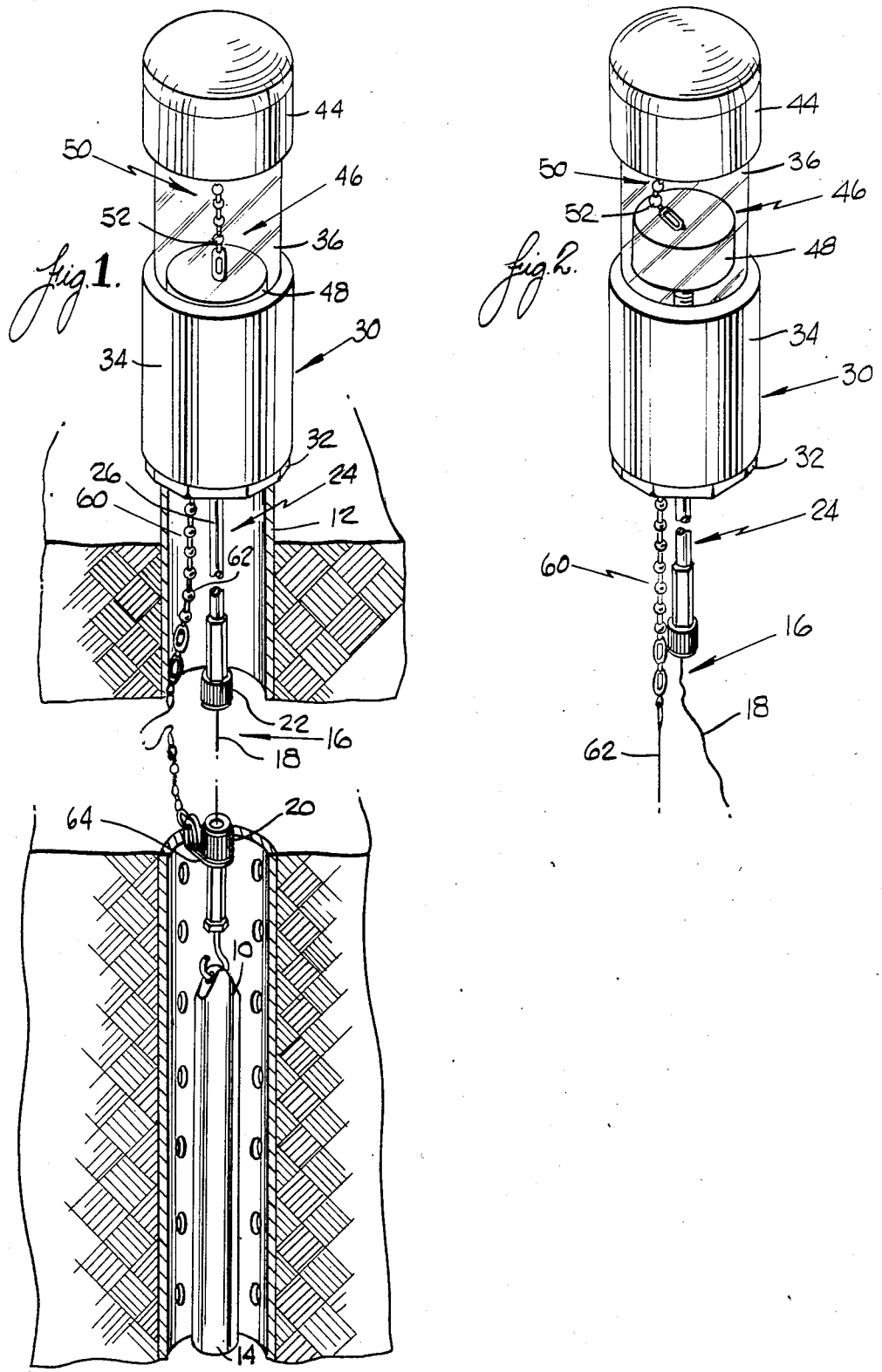

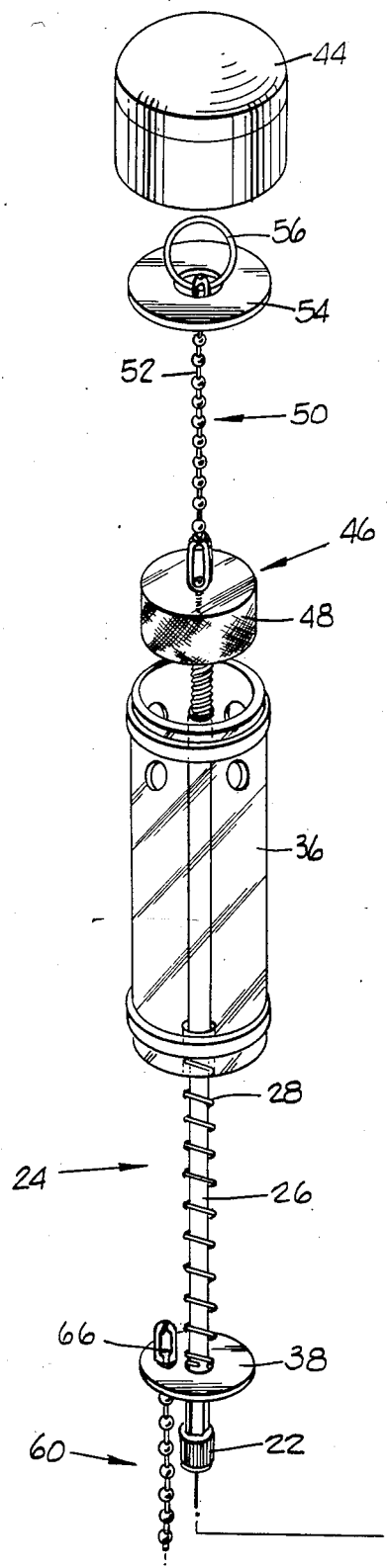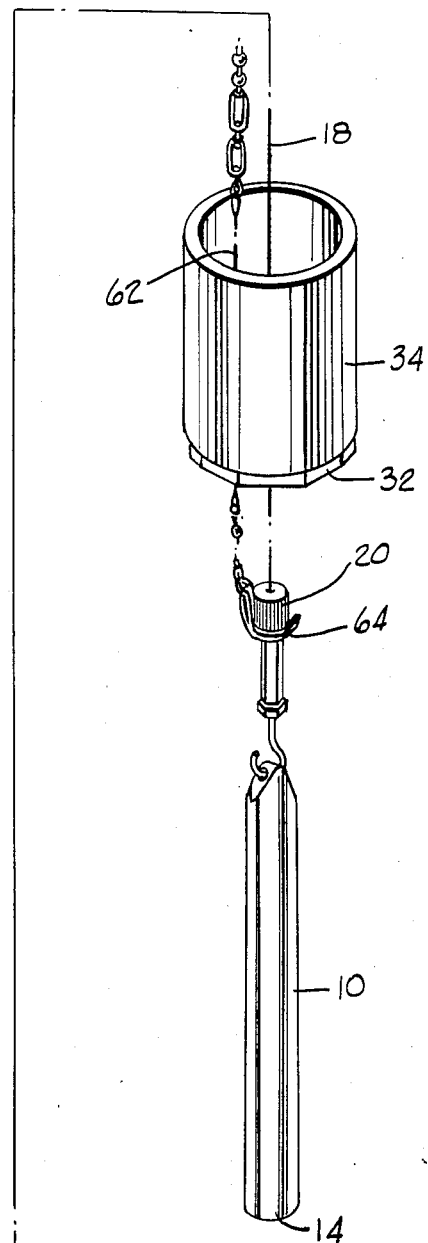
Fig. 3.

U.S. Patent  Jul. 21, 1987  Sheet 3 of 3  4,682,156
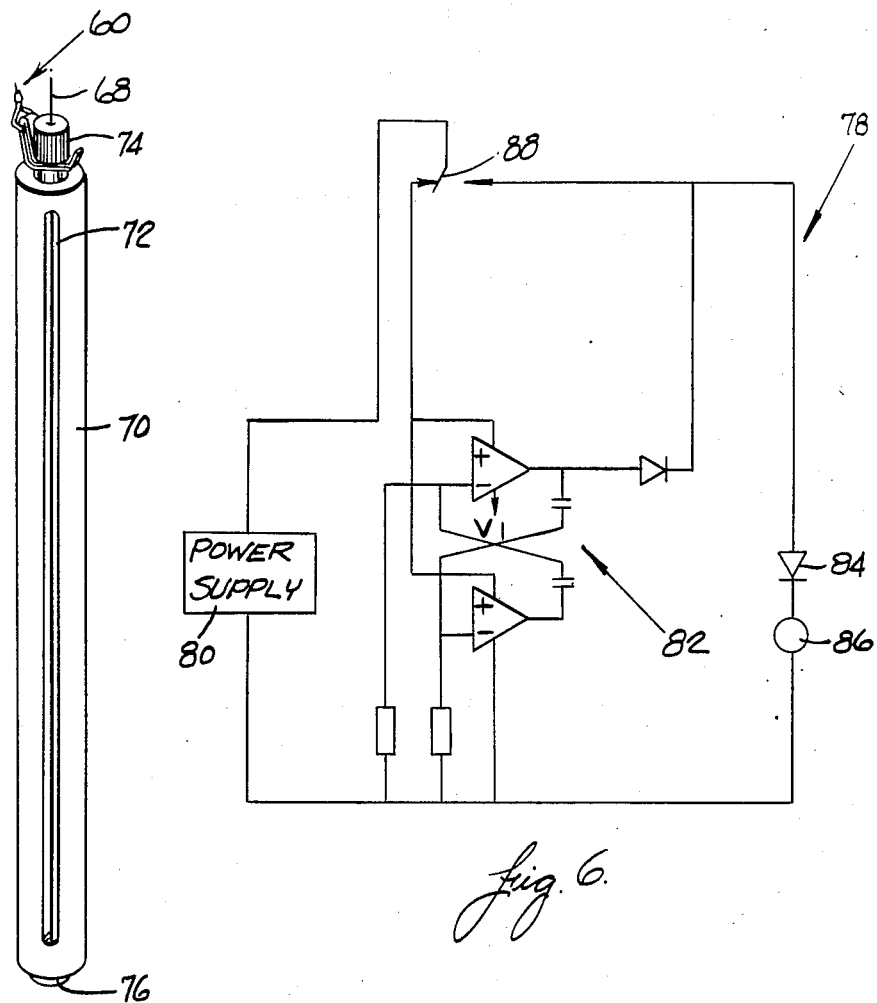
fig. 6.
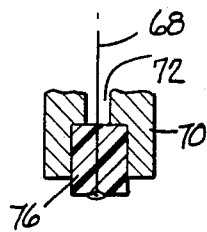
fig. 4.
fig. 5.

SOLVENT DETECTOR

FIELD OF THE INVENTION

The present invention relates to method and apparatus for detecting solvents including hydrocarbons, particularly gasoline.

BACKGROUND INFORMATION

Concern over the leakage of gasoline into water supplies has increased in recent years. At gasoline service stations there is the potential problem of a gasoline leak from the tank housing the gasoline. If a leak should occur, gasoline could enter and contaminate the water supply.

Because of the serious consequences associated with gasoline contaminated water, it would be very beneficial to be able to detect if such contamination occurred. In one known commercially available apparatus for sensing the presence of hydrocarbons, nitrogen under pressure is utilized. This nitrogen is located in a pressurized tube. When the pressurized tube is perforated because of the presence of hydrocarbons, a drop in pressure is sensed indicating that hydrocarbons are present. However, such an apparatus is relatively expensive and requires that the pressure be maintained, which pressure could be accidently lost by an unexpected perforation during handling, for example.

Another known device for detecting hydrocarbons utilizes a sequenced styrene-butadiene copolymer strip which is connected at one end to the device to place a spring under tension. This hydrocarbon strip deterition triggers an indication of the presence of hydrocarbons. This device is not connected to a well casing nor does it show the ability to provide hydrocarbon detection at different locations along a relatively great length because the hydrocarbon detecting strip is typically 20-25 centimeters long.

To overcome the deficiencies of the prior art, the present invention is directed primarily to detecting the presence of gasoline in a fully perforated well casing installed in the ground. In that regard, the sensing element of the present invention is a rod or filament which is capable of supporting a weight and having a maximum length of tens of feet.

SUMMARY OF THE INVENTION

An apparatus is disclosed for detecting the presence of hydrocarbon-containing fluids, such as gasoline. The apparatus includes a sensing element which is soluble in hydrocarbons. The sensing element is connected to a mass or weight at one end and to a weighing assembly at a second end. An alarm indicator is attached to the weighing assembly. When hydrocarbons contact the sensing element, the sensing element dissolves or separates so that the weight is detached from the weighing assembly. This separation is detected by the weighing assembly, which results in an indication that hydrocarbons are present.

More particularly, the sensing element is a hydrocarbon-soluble plastic rod or filament having a relatively small diameter and which can have a length of tens of feet for placement in a well. In one embodiment, a first end of the sensing rod is connected to a first end of the weight. The second end of the weight is free and able to be placed at a desired depth in the well. A second end of the sensing rod is connected to a weighing mechanism, which includes a push rod and a coiled spring. An alarm indicator is connected to one end of the push rod and includes a readily visible colored marker for indicating the presence of hydrocarbons. The push rod is inserted through the coiled spring and the spring is located adjacent to the marker. The spring and a portion of the push rod are located in a housing. The housing includes a connector for fastening the apparatus to a well casing.

In another embodiment, the weight is drilled and slotted to receive the sensing rod which is inserted axially through the weight and connected to the bottom end of the weight. This configuration permits use of the hydrocarbon sensing capability at the bottom portions of a well without regard to the length of the weight.

The apparatus further includes a weight or mass catch assembly which is connected to one end of the weight. The opposite end of the weight catch assembly is attached to a support washer located in the housing. When the sensing element separates due to the presence of hydrocarbon, the weight catch assembly acts to prevent the weight from completely separating from the apparatus. Because the weight catch assembly is not connected to the weighing assembly, the catching of the weight does not affect the operation of the alarm indicator.

The apparatus also includes a testing assembly which can be used by an operator to determine whether the apparatus is functioning properly. The testing assembly is connected to the alarm indicator and can be grasped by the operator to pull the weight upwardly so as to cause the alarm indicator to be readily seen Based on the foregoing description, a number of objectives of the present invention can be readily understood. A hydrocarbon detecting device is provided for sensing the presence of hydrocarbons and giving an immediate indication that hydrocarbons are present. The device has a housing which is readily connectable to a well casing into which a hydrocarbon-soluble sensing element is placed. The sensing element is a relatively thin rod which can be of any length and, therefore, the device can be used in wells of significant depth. When hydrocarbons are detected due to a change in the sensing of a weight, which is separated from a weighing mechanism, the weight is not lost but remains connected to the device through the use of a catch assembly. The apparatus also includes testing means for assuring that the apparatus is working properly and that the weight is properly connected to the sensing element. Lastly, the apparatus functions efficiently and yet is simply constructed to provide a relatively inexpensive device for sensing hydrocarbons.

Additional advantages of the present invention will become readily apparent from the following discussion when taken in conjunction with the accompanying drawings.

BRIEF DESCRIPTION OF THE DRAWINGS

Fig. 1 is a perspective view of the hydrocarbon detector of the present invention located in a well casing;

FIG. 2 is a further perspective view of the hydrocarbon detector of the present invention showing a separation in the sensing element resulting in an alarm indication that hydrocarbons are present;

FIG. 3 is an exploded view of the elements of the hydrocarbon detector shown in FIGS. 1 and 2;

FIG. 4 shows another embodiment of the mass having a slot;

FIG. 5 illustrates the bottom portion of the mass of FIG. 4 showing the connection of the sensing element to the mass; and FIG. 6 illustrates an electrical schematic of an alarm indicator which can be added to the alarm indicator shown in FIGS. 1-3.

DETAILED DESCRIPTION OF THE PREFERRED EMBODIMENTS

In accordance with the present invention, a solvent detector is provided for use primarily with a fully perforated well casing provided in the ground. With reference in particular to FIGS. 1 and 3, the detector includes a mass 10 which is the first part of the detector to be placed into the well casing 12. The mass 10 includes a free end 14, which is located at one end of the detector. The opposite end of the mass 10 is connected to a sensing assembly 16. The sensing assembly 16 includes a thin plastic rod or filament 18 which is soluble in hydrocarbons. The diameter of the rod depends upon the weight of the mass 10 which it supports. Typically, the diameter of the rod 18 is about 0.030 inches and it is expected that the diameter will not be greater than about 0.5 inches for the anticipated applications of the present invention. The rod 18 may be of many different lengths, depending upon the depth or extent of the well into which the apparatus is placed.

The sensing assembly 16 also includes a pair of fasteners 20, 22. A first fastener 20 is connected to the mass 10, while a second fastener 22 is connected to a weighing assembly 24. In one embodiment the fasteners 20, 22 are hollow and receive the rod 18 therethrough. After the fasteners 20, 22 are held along a desired length of the rod 18, the ends of the rod 18 are enlarged so that the fasteners 20, 22 cannot move past the ends of the rod 18.

The weighing assembly 24 includes a push rod 26 and a spring 28. The push rod 26 is connected to the second fastener 22 to provide the interconnection among the mass 10, the sensing rod 18, and the weighing assembly 24. The end of the push rod 26, opposite that end connected to the sensing rod 18, has the spring 28 coiled therearound.

A portion of the push rod 26 is received in a housing 30. The housing 30 includes a well casing connector 32, an opaque tube 34, and a transparent tube 36. The well casing connector 32 is used to connect the hydrocarbon detector to the top of the well casing 12 while the mass 10 can be suspended at a desired depth in the well, using the sensing rod 18, depending upon the length of the sensing rod 18, which is based upon the desired depth to which the mass 10 will be located. Located and held within the opaque tube 34 is a support washer 38. The well casing connector 32 has an inner diameter such that the support washer 38 rests thereon and is held in the housing 30. The push rod 26 is of a diameter such that it is received through the hole in the support washer 38.

The transparent tube 36 is connected to the opaque tube 34 and has a number of openings adjacent to the top thereof for venting moisture. A cap 44 is placed over the top of the transparent tube 36 and prevents unwanted debris of other material from entering into the housing 30.

In connection with providing an indication to the user that hydrocarbons are present, an alarm indicator 46 is utilized. The alarm indicator 46 is connected to the end of push rod 26 having the spring 28 coiled thereabout. In one embodiment, the alarm indicator 46 includes a highly visible or colorful marker 48, which comes into view when hydrocarbons are sensed in the well.

The hydrocarbon detector of the present invention also includes a testing assembly 50 to determine whether the rod 18 is still continuous and the mass 10 is still connected to the rod 18. Additionally, the testing assembly 50 is used to verify that the marker 48 is readily visible should hydrocarbons be detected and that the push rod 26 is free to move. The testing assembly 50 includes a linking member 52, which is connected at one of its ends to the alarm indicator 46. The opposite end of the linking member is positioned through the hole in a washer 54 and connected thereto by means of a ring 56, or the like. To utilize the testing assembly 50, the cap 44 is removed from the housing 30 and the ring 56 is grasped by the user and pulled upwardly so as to cause movement of the alarm indicator 46. This movement causes the alarm indicator 46 to be moved away from being surrounded by the opaque tube 34 to be readily visible through the transparent tube 36. In such a manner also, the user can determine whether the mass 10 is still properly connected to the rod 18.

The hydrocarbon detector additionally includes a mass catch assembly 60. The assembly 60 includes an attaching line or member 62 which interconnects the mass 10 and the support washer 38. This interconnection is accomplished by means of connectors 64, 66. A first connector 64 joins the attaching line 62 to the mass 10, at the same end to which the sensing rod 18 is connected. A second connector 66 joins the opposite end of the attaching line 62 to the support washer 38. This is accomplished by having the second connector 66 received through a hole formed in the support washer 38. The end of the second connector 66 is greater than the support washer hole so that the second connector 66 remains joined to the support washer 38.

In using the hydrocarbon detector, a length of sensing rod is chosen depending upon the depth to which the mass 10 is to be located in the well casing 12. The sensing rod 18 having this desired length is connected between the push rod 26 and the mass 10. The mass 10 is lowered into the well casing 12 and the sensing rod 18 eventually becomes taut and the mass 10 is located at a desired place in the well. Also, with the sensing rod 18 becoming taut, the weight pulls the push rod 26 downwardly so that the alarm indicator 46 is located within or surrounded by the opaque tube 34 of the housing 30. In that regard, the spring 28 is unable to pass through the hole in the support washer 38, but instead contacts the support washer 38 resulting in a compression of the spring 28 and the supporting of the mass 10 by the weighing mechanism 24 and the support washer 38.

The housing 30 is connected to the well casing 12 by means of the well casing connector 32. The connector 32 can be threaded to the well casing 12 or force fitted thereto, or the like.

In the case in which gasoline or other hydrocarbon is present in the well casing and contacts the sensing rod 18, such hydrocarbons act to dissolve or break the hydrocarbon-soluble rod 18. This dissolution, in the presence of hydrocarbons, occurs after a relatively short period of time. With the breaking of the sensing rod 18 along the portion thereof which comes in contact with the hydrocarbons, the mass 10 is no longer connected to the weighing assembly 24. Because the mass 10 is no longer connected to the weighing assembly 24, the weight holding the push rod 26 down and keeping the spring 28 compressed is no longer present. As a result, the spring 28 returns to its non-compressed state causing the push rod 26 to move upwardly. In so doing, because the alarm indicator 46 is attached to the end of the push rod 26, the alarm indicator 46 moves away from being surrounded by the opaque tube 34 to being surrounded by the transparent tube 36, as can be seen in FIG. 2. Because of the transparency of the tube 36, the user of the hydrocarbon detector can see that an alarm indication is provided indicating that hydrocarbons are present and have dissolved the sensing rod 18.

Although the sensing rod 18 no longer connects the mass 10 and the weighing assembly 24, the mass catch assembly 60 acts to hold the mass 10 to the housing 30. More specifically, the non-free end of the mass 10 is connected to the support washer 38 by the attaching line 62. Consequently, even though hydrocarbons have been detected, the mass 10 is not lost or dropped into the well casing 12.

In another embodiment of the invention, with reference to FIGS. 4 and 5, a sensing element or filament 68 is inserted through a mass or weight 70 having a hollowed slot 72 formed therethrough. The slot 72 extends substantially throughout the longitudinal extent of the filament 68. A fastener 74 is connected to the top end of the mass 70 as guide for the filament 68. The fastener 74 has a hole therethrough for receiving the filament 68. The fastener 74 is also used for connecting a mass catch assembly 60. At the opposite or bottom end of the mass 70 an insert 76 is provided. The insert 76 is fixedly held in the bottom of the mass 70 and includes a hole through which the filament 68 is enlarged after receipt through the insert hole for retaining the end of the filament 68 at the insert 76.

With respect to the detection of hydrocarbon adjacent to the mass 70, the liquid containing the hydrocarbon is able to pass through the slot 72 for contacting the sensing element 68. By means of this embodiment, the mass 70 can be located at the bottom of a well casing 12 and any hydrocarbon found at the bottom of the well casing 12 can be detected by the sensing rod 68 since it extends to being immediately adjacent to the well casing bottom.

In still another embodiment of the invention, an electrical alarm indicator 78 is used together with the alarm indicator 46. With reference specifically to FIG. 6, the electrical alarm indicator 78 includes a power supply 80 used to provide electrical power for the indicator 78. The electrical alarm indicator 78 also includes a pulse generator 82 and, preferably, both a visual indicator 84 and an audio indicator 86. The indicator 68 additionally includes a switch 88. The switch 88 is operatively connected to the weighing assembly 24 so that, when the push rod 26 is pulled downwardly by the mass 10, the switch 88 is at a first state and when the push rod 26 is disconnected from the mass 10, the switch 88 is at a second state. In particular, during normal operation or when hydrocarbons are not present, the switch 88 has a first state whereby power is applied to the pulse generator 82. With the application of power to the pulse generator 82, an intermittent or pulsing signal is applied to the visual indicator 84 and the audio indicator 86 thereby causing an intermittent lighting or flashing of the visual indicator 84 and an intermittent sounding of the audio indicator 86. These visual and audio indications inform the user that no hydrocarbons are present, power is properly applied, the conducting cable is continuous, the alarm components are functioning properly, and the switch 88 is at the appropriate position.

When hydrocarbons are indicated and the sensing rod 18 breaks, the push rod 26 is released upwardly to cause the switch 88 to change to its second state. In the second state, power is no longer applied to the pulse generator 82, but is directly applied to the visual indicator 84 and the audio indicator 86. As a consequence, a continuously lit visual indicator 74 is provided, as well as a continuously sounding audio indicator 86. Such alarms indicate to the user that hydrocarbons are present.

In view of the foregoing detailed discussion of the present invention, a number of advantages of the invention are readily seen. An apparatus is provided and a method disclosed for efficiently and effectively detecting the presence of hydrocarbons in a fluid. The invention is easily positioned in a well casing and connected thereto for providing at least a visual indication of whether or not hydrocarbons are present. The present invention relies on the use of a hydrocarbon-soluble plastic rod which can be of any length for use in wells of varying depths. In addition, the present invention uses a mass and weighing assembly for use in determining whether hydrocarbons are present. The mass is not lost or released from the detector when hydrocarbons are present and the sensing rod disconnects the weighing assembly and the mass. Instead, a mass catch assembly holds the mass to the detector. Finally, a testing assembly is provided as part of the apparatus so that the user can ascertain whether the apparatus is functioning properly.

Although the present invention has been described with reference to certain embodiments, it should be appreciated that further modifications can be effected within the spirit and scope of the invention.

What is claimed is:

1. A solvent detecting apparatus adapted for use partially within a well casing, comprising:
   a sensing element that is dissolvable in the presence of a solvent, said sensing element constituting a major portion of the length of that part of the apparatus within the well casing, wherein when a solvent contacts any portion of said sensing element at least part of the contacted portion of the sensing element dissolves;
   a weighing assembly connected to a portion of said sensing element, said weighing assembly being movable between a first position and a second position;
   a mass connected to a portion of said sensing element, said mass causing said weighing assembly to be located at said first position of said weighing assembly, said mass being separate from said sensing element and being made of a material different from that of said sensing element;
   an alarm indicating means operatively connected to said weighing assembly for providing an indication of the presence of a solvent when any portion of said sensing element dissolves in response to contact with a solvent.

2. An apparatus, as claimed in claim 1, further including:
   a housing having connecting means for connecting said housing to a well casing.

3. An apparatus, as claimed in claim 2, further including:

mass catch means for connecting said mass and said housing together, but being detached from said weighing assembly, so that said mass is not detached from the remaining parts of the apparatus when the solvent is detected.

4. An apparatus, as claimed in claim 3, wherein: said mass catch means includes an attaching member and a pair of connectors for connecting said attaching member to said mass and to said housing.

5. An apparatus, as claimed in claim 2, wherein: said weighing assembly includes a push rod and a spring coiled around said push rod, at least a portion of said push rod being positioned in said housing.

6. An apparatus, as claimed in claim 2, wherein: said housing includes an opaque member and a transparent member, said opaque member surrounding said alarm indicating means when said weighing assembly is in its first position and said transparent member surrounding said alarm indicator means when said weighing assembly is in its second position.

7. An apparatus, as claimed in claim 2, further including:
a support washer within said housing, said support washer having a hole for receiving a portion of said weighing assembly.

8. An apparatus, as claimed in claim 7, wherein: said weighing assembly includes a push rod and a spring, said push rod being received through said hole in said support washer and said spring being compressed against said support washer when said sensing element interconnects said mass and said push rod.

9. An apparatus, as claimed in claim 1, wherein: said mass includes a free end and a non-free end, said non-free end being connected to said sensing element and said free end being detached from the remaining parts of the apparatus.

10. An apparatus, as claimed in claim 1, wherein: said sensing element being located between said mass and said weighing assembly and said sensing element extending substantially the entire length of the well casing.

11. An apparatus, as claimed in claim 1, wherein: said sensing element has a portion located substantially along the longitudinal extent of said mass.

12. An apparatus, as claimed in claim 1, wherein: said sensing element has a portion positioned within said mass.

13. An apparatus, as claimed in claim 1, further including:
testing means for moving said mass and for use in changing the position of said weighing assembly to verify that the apparatus is functioning properly.

14. An apparatus, as claimed in claim 13, wherein: said testing means includes first means connected to said alarm indicator means; and
second means connected to said first means for use in pulling said alarm indicator means.

15. An apparatus, as claimed in claim 1, wherein: said sensing element is a plastic rod less than about 0.5 inches in diameter.

16. An apparatus, as claimed in claim 15, wherein: said rod is about 0.030 inches in diameter.

17. An apparatus, as claimed in claim 1, wherein: said alarm indicator means includes a marker connected to said weighing assembly, said marker being readily visible when the solvent is detected by the apparatus.

18. An apparatus, as claimed in claim 1, wherein: said alarm indicator means includes a flashing light in the absence of hydrocarbon being detected by the apparatus and a continuously lit light when the solvent is detected by the apparatus.

19. An apparatus, as claimed in claim 1, wherein: said alarm indicator means includes audio means for providing a sound indicating that the solvent is present.

20. A method for detecting a solvent in a well casing with a solvent detecting apparatus adapted for use partially within the casing, comprising:
providing a weighing assembly for movement between a first position and a second position;
providing a sensing element separate from said mass and being made of a lighter material than said mass, wherein said sensing element constitutes a major portion of the length of that part of the apparatus within the well casing;
interconnecting said mass and said weighing assembly using said sensing element;
placing said mass below at least portions of said sensing element for locating said sensing element in an area for detecting the presence of the solvent;
using said mass to move said weighing assembly from said first position to said second position;
sensing whether the solvent is present in the area of location of said sensing element; and
indicating whether the solvent is present using the movement of said weighing assembly.

21. A method, as claimed in claim 20, wherein: positioning at least a portion of said sensing element through said mass.

22. A method, as claimed in claim 20, wherein: terminating one end of said sensing element adjacent to a top end of said mass.

23. A method, as claimed in claim 20, wherein: said mass has a non-free end and a free end, and the method includes positioning said free end below said sensing element.

24. A method, as claimed in claim 23, wherein: providing an attachment to said non-free end of said mass;
causing said sensing element to separate when hydrocarbons are detected; and
holding said mass using said attachment after separation of said sensing element.

25. A method, as claimed in claim 20, wherein: providing a housing for receiving at least a portion of said weighing assembly; and
connecting said housing to a well casing such that an indication can be provided when hydrocarbons are detected by said sensing element.

26. A method, as claimed in claim 20, wherein: said weighing assembly includes a push rod and a spring, and the method further includes compressing said spring using said mass to move said weighing assembly to said second position; and
releasing the compression in said spring to move said weighing assembly to said first position.

27. A method, as claimed in claim 20, further including the step of:
pulling on said weighing assembly to raise said mass to check the operation of the apparatus.

* * * * *

UNITED STATES PATENT AND TRADEMARK OFFICE
CERTIFICATE OF CORRECTION

PATENT NO. : 4,682,156

DATED : July 21, 1987

INVENTOR(S) : H. Kent Wainwright

It is certified that error appears in the above—identified patent and that said Letters Patent is hereby corrected as shown below:

At Column 1, line 32, delete "deterition" and insert therefor --deteriorates when contacted by hydrocarbons and such deterioration--

At Column 2, line 32, insert a period after "seen".

At Column 3, line 62, delete "of" and substitute therefor --or--.

Signed and Sealed this

First Day of March, 1988

Attest:

DONALD J. QUIGG

*Attesting Officer*   *Commissioner of Patents and Trademarks*